United States Patent [19]

Ruley et al.

[11] Patent Number: 5,364,783
[45] Date of Patent: Nov. 15, 1994

[54] RETROVIRUS PROMOTER-TRAP VECTORS

[75] Inventors: H. Earl Ruley, Winchester; Harold von Melchner, Boston, both of Mass.

[73] Assignee: Massachusetts Institute of Technology, Cambridge, Mass.

[21] Appl. No.: 523,041

[22] Filed: May 14, 1990

[51] Int. Cl.⁵ .................. C12N 7/01; C12N 15/11; C12N 15/65
[52] U.S. Cl. ................ 435/235.1; 435/172.3; 536/23.1; 536/24.33; 935/32
[58] Field of Search ............ 435/235.1, 172.3; 536/27, 23.1, 24.33; 935/32

[56] References Cited

U.S. PATENT DOCUMENTS

| | | | |
|---|---|---|---|
| 4,738,922 | 4/1988 | Haseltine et al. | 435/69.1 |
| 4,952,499 | 8/1990 | Cantor et al. | 435/69.1 |
| 4,980,289 | 12/1990 | Temin et al. | 435/69.1 |
| 4,999,421 | 3/1991 | Brunck et al. | 514/25 |

OTHER PUBLICATIONS von Melchner et al., "Identification of Cellular Promoters", *J. Virology* 63: 3227–3233, Aug. 1989.
Lobel et al., "Construction and Recovery of Viable Retroviral Gemomes . . . ", *Science* 228: 329–332, 19 Apr. 1985.
Reik et al., "Replication-competent Maloney murine leukemia virus . . . " *PNAS* 82:1141–1145, Feb. 1985.
von Melchner et al. 1990. Proc. Natl. Acad. Sci. USA 87,3733–3737. Dougherty et al. 1987. Proc. Natl. Acad Sci USA. 84,1197–1201.
Hiller et al. 1988 Molec. Cellular Bio. 8,3298–3302 Murphy et al. 1989. J. Virol. 63,319–327.
Kucherlapati et al. 1988, J. Cell. Biochem. Supp 12B. 0. 198, #H306.

Primary Examiner—Stephen G. Walsh
Attorney, Agent, or Firm—Edward R. Gates

[57] ABSTRACT

Retroviruses are used as genetic tools to isolate transcriptionally active chromosomal regions. The retroviruses have a promoterless protein coding sequence located in U3 or U5. The retroviruses may be used to infect cells under conditions which permit selection for instances when the retrovirus integrates in close proximity to and under the control of a cellular promoter. The promoter and its associated gene then may be identified and isolated. In this manner, the retroviruses function as promoter-traps. Related methods and products including vectors, kits and assays provided.

14 Claims, 6 Drawing Sheets

|       | FLANKING CELLULAR DNA | | PROVIRUS |
|-------|---|---|---|
| U3    | | AA | TGAAAGACCCCACCTGTAGGTTTGGCAA |
| P3a   | ACCTTACAAAAGATGGGTGTACGCTCTCTTTTCAGAGTAAGTAGTGTTAA | --- | TGAAAGACCCCACCTGTAGGTTTGGCAA |
| P3b   | ATGTCTTTGG AAAAGGATATTAACTTTGCAAGTTCTGGGCTGACTTGTAT | --- | TGAAAGACCCCACCTGTAGGTTTGGCAA |
| P7    | GGTGCGTCCG AGTACTCTAAGGGTTTAACTTACTGATTAAAGTCTTCTCT | --- | TGAAAGACCCCACCTGTAGGTTTGGCAA |
| Ψ7a   | GCTTATGGAG ACTGAAAATAGGCTAAGACCTCTATT TGCCCAAAAATGTC | --- | TG CGGT ACCCCACCTGTAGGTTTGGCAA |
| Ψ7b   | TTATAGACCA GGGTGGCCTCGAACGTAAAATCCGCCTCTGCCACCC | --- | TGAAAGACCCCACCTGTAGGTTTGGCAA |
| Ψ9    | GGTAGACGCG GCTCCGGGGCCTTCCGCTTTACACACTTGTGAGCGGCTCC | --- | TGAAAGACCCCACCTGTAGGTTTGGCAA |

FIG. 9

RETROVIRUS PROMOTER-TRAP VECTORS

FIELD OF THE INVENTION

This invention relates to specially constructed retroviruses, retrovirally transduced cells and related methods, including methods permitting the identification and isolation of mammalian promoters and associated genes.

BACKGROUND OF THE INVENTION

The human genome contains approximately $3 \times 10^9$ nucleotides, but only about 10,000–40,000 genes expressed at one time in any given cell type. Massive research efforts have been directed to identifying and isolating genes and their related regulatory DNA. These efforts have been confounded by the limitations of existing technology.

Transcription of eukaryotic genes is regulated by cis-acting DNA sequences. Promoters are located immediately upstream of transcriptional start sites and control transcriptional initiation by RNA polymerase. Enhancer elements increase the rate of transcriptional initiation, and to a certain extent, function irrespective of their position or orientation.

Most promoters have been isolated from genomic libraries using cDNA probes to identify sequences downstream of the transcriptional start site and by testing nearby sequences for promoter activity. However, isolating cellular promoters can be difficult because nearly full-length cDNA clones may be required to identify genomic sequences near the sites of transcriptional initiation, and transcribed genomic sequences may be hard to distinguish from untranscribed pseudogenes.

Several investigators have used moveable elements to isolate cellular promoters or enhancers by linking random DNA fragments to the coding sequence of a selectable marker transforming or antibiotic resistance genes), introducing the DNA into recipient cells and selecting for cell clones that result if the gene is expressed. However, this approach suffers from several limitations that the present strategy avoids. First, DNA-mediated gene transfer is not the most efficient form of transduction, particularly in certain cell types. Second, introduced genes are frequently amplified in cells surviving selection. This increases background and necessitates screening multiple clones or performing secondary transfections in order to identify clones containing only one gene copy. Third, potential promoter/enhancer elements identified following DNA transfer are not expressed in their normal chromosomal locations.

Transfected enhancerless genes have been used to identify transcriptionally active chromosome regions. In some cases, expression appeared to be regulated in a tissue specific manner. Similarly, integration specific activation of provital genes has been observed in cells in which the LTR is transcriptionally inactive. However, cloning transcriptional activators using this approach is difficult, because elements such as enhancers may be located at considerable distance and on either side of the integrants.

The present invention exploits the ability of retroviruses to move genes into random sites of mammalian genomes.

Retroviruses are RNA viruses that replicate through a DNA intermediate. Flanking the ends of the viral RNA genome are short sequence repeats (R) and unique sequences (U5 and U3) that control DNA synthesis, integration, transcription, and RNA processing. Between the control regions are coding sequences for the major structural proteins of the virus particle (gag and env) and for enzymes found in particles (pol, protease, reverse transcriptase and integrase) (FIG. 1).

Shortly after infection, viral RNA is converted into DNA by reverse transcriptase. Prior to integration, terminal sequences of the viral genome are duplicated such that the retroviral genome is flanked by long terminal repeats (LTRs), each containing the U3, R and U5 regions. Then integration occurs.

The exact mechanism of integration is unclear. There is evidence that formation of circular molecules with 2 tandem LTRs creates cis-acting recognition sequences for the enzymes catalyzing integration. However, several investigators have shown that linear viral DNA can integrate directly without forming a circularized intermediate, at least in vitro.

LTR sequences are maintained in the integrated retrovirus, also termed —provirus—, except that two nucleotides (nt) are lost from each end. Cellular DNA sequences also are unaltered except that upon integration, 4–6 nt are duplicated such that the provirus is flanked at each end by 4–6 bp repeats. As a provirus, the retroviral genome is replicated with cellular DNA and transcribed as a cellular gene. Provirus transcription is controlled by promoter/enhancer sequences located in the U3 region of the 5' LTR. Polyadenylated transcripts initiate at the junction between U3 and R (cap site) in the 5' LTR and terminate in R of the 3' LTR that contains the signal for polyadenylation. RNA is synthesized by cellular RNA polymerase II and processed by the cellular enzymes. Full-length (genomic) RNA is transported from the nucleus to the cytoplasm and either packaged into virus particles that bud from the cell or are translated to yield gag and pol proteins. A fraction of the RNA is spliced to yield mRNA encoding env.

It is possible to adapt retroviruses to transduce genes into mammalian genomes. Provided that certain control sequences within the LTRs remain unaltered [Murphy, 1989 #76; Dougherty, 1987 #134], the retroviral genome can be deleted without impairing its ability to replicate in cells that express proteins necessary for reverse transcription, integration and particle formation. For this, vector DNA is transfected into cell lines that contain complete retroviral genomes or helper viruses. The helper viruses are constructed so that they cannot assemble into particles, due to a small deletion encompassing a sequence ($\Psi$) between U5 and gag. Since the vector DNA does not contain the $\Psi$ deletion, recombinant transcripts are packaged and expelled from the cells as virus particles. In addition to $\Psi$, gag sequences also enhance the ability of the vectors to be packaged.

Retroviruses appear to integrate randomly throughout the genome although about one fifth of all integrations have been reported to involve highly preferred sites. Integrations sometimes results in mutations that either inactivate or augment expression of genes in the vicinity of the provirus. Gene inactivation may be caused by insertions into exons that interrupt open reading frames or introns that alter normal splicing patterns. Activation of genes adjacent to the provirus involves transcriptional enhancement either by upstream U3 promoters or nearby U3 enhancers.

Retroviruses have been used both as probes for transcriptionally active chromosomal regions and as insertional mutagens. However, several factors have undermined the practical use of retroviruses as genetic tools to study mammalian organisms. First, large genomes ($3 \times 10^9$ nucleotides) necessitate screening large numbers of integrants in order to detect mutations in any specific gene. Second, mutations resulting from provirus integration are generally recessive, since most mammalian genomes are diploid. Third, enhancers in the LTRs may influence the expression of adjacent genes, and thus interfere with detecting cellular sequences that regulate transcription in a tissue specific manner. Finally, 3' RNA processing signals and AUG codons within the lefthand LTR interfere with activation of proviral genes by nearby cellular promoters. As a consequence, retroviruses have been used only to a limited extent, for example: (i) as enhancer traps, by using cell lines in which the vital enhancer is inactive or by using viruses in which the vital enhancer has been deleted, or (ii) as gene traps which rely on RNA splicing to remove intervening viral sequences.

SUMMARY OF THE INVENTION

The invention involves the development of novel retroviruses useful in isolating transcriptionally active chromosomal regions. The retroviruses have a promoterless protein coding sequence positioned in a control region, preferably in U3. The promoterless protein coding sequence can be located so that it does not impair the ability of the retrovirus to be passaged. When cells are infected with the retroviruses of the invention, the promoterless protein coding sequence is duplicated along with the control regions, prior to integration. The duplicated protein coding sequence is located close to an end of the integrated provirus. Cell clones containing the provirus then may be selected based upon the expression of the duplicated protein coding sequence, expression indicating that the duplicated sequence is positioned close to and under the control of an endogenous promoter.

The retroviruses of the invention can be enhancerless so that expression of adjacent cellular sequences is not affected.

In another aspect of the invention nucleic acids are provided. The nucleic acids have a promoterless protein coding sequence flanked by integration sequences. These integration sequences may be derived from viruses or proviruses, or they may be synthetically derived. The nucleic acid can be nonintegrated linear or circular DNA, single or double stranded, and also may be integrated into genomic DNA. If integrated into genomic DNA, the protein coding sequence preferably is under the control of an endogenous promoter. Most preferably the nucleic acids are proviruses having a promoterless protein coding sequence located within an LTR.

The invention also provides cells including the retroviruses and/or nucleic acids of the invention. Such cells may contain in their genomic DNA an endogenous promoter separated from a protein coding sequence by an integration sequence. Preferably, the endogenous promoter controls the expression of the protein coding sequence. Most preferably the cells contain proviruses derived from the retroviruses of the invention.

The cells may be used for example in connection with identifying and isolating promoters and genes, conducting drug screening assays, studying gene expression during development and studying gene function. The cells in preferred embodiments are mammalian. In one embodiment of the invention, the cells are part of a transgenic animal.

According to other aspects of the invention, methods for putting a protein coding sequence under the control of an endogenous promoter are provided. A promoterless protein coding sequence sandwiched between DNA integration sequences is introduced into genomic DNA in a manner such that the expression of the protein coding sequence is regulated by an endogenous promoter. Preferably, the protein coding sequence is within the a LTR of a provirus and is introduced into cellular genomic DNA by infection with a retrovirus containing a promoterless protein coding sequence in a control region of the retrovirus.

To identify, isolate and sequence promoters, cells in which the protein coding sequence is regulated by an endogenous promoter may be selected based upon the expression of the protein coding sequence. The promoter regulating expression then may be isolated from substantially all of the genomic DNA, and subsequently sequenced.

Isolation of promoters may be accomplished by a variety of methods, including PCR amplification of the promoter, preferably using primers to the protein coding sequence. According to this aspect of the invention, genomic DNA including the nucleic acids of the invention is cleaved into small segments, and then these small segments are circularized. The circularized segments then are amplified by PCR using a pair of primers capable of hybridizing to the protein coding sequence. In this manner, only segments containing promoters are amplified.

According to another aspect of the invention, methods for assaying substances are provided. The cells of the invention may be treated with a substance (such as a peptide, factor or chemical) to determine whether that substance affects the ability of the promoter to initiate transcription of the protein coding sequence. The cells of the invention also may be treated with oncogenes in the presence of a substance to determine whether that substance acts to block oncogenesis.

Probes capable of hybridizing to genomic promoters or portions thereof also are provided. These probes may be prepared as described above, and may be used for a variety of purposes, including probes to locate the position of endogenous promoters in genomic DNA, promoter inserts for controlling expression in vectors, and probes to locate endogenous genes.

Probes capable of hybridizing to genes or portions thereof also are provided. Once promoters or flanking regions are isolated, genes associated with such promoters may be isolated. According to one preferred method, a probe corresponding to the genomic DNA between an endogenous promoter and a provirus of the invention is prepared. Such a probe may be used to identify and isolate a gene from cDNA libraries.

Kits for performing certain methods of the invention also are provided. The kits include a container storing retroviruses with a protein coding sequence in their control region, and a container storing primers capable of hybridizing to that protein coding sequence. The kits also may include a container storing an enzyme capable of cleaving the protein coding sequence at a particular site.

BRIEF DESCRIPTION OF THE DRAWINGS

FIG. 9 is the DNA sequences for six segments of genomic DNA flanking proviral integrants from cells having expressed protein coding sequences;

DESCRIPTION OF THE PREFERRED EMBODIMENT

Figure 1:
FIG. 1 is a schematic diagram of the genome of prior art retroviruses.

The term "retrovirus" refers to any RNA virus that replicates through a DNA intermediate. Such viruses can include those that require the presence of other viruses, such as helper viruses, to be passaged. Thus, retroviruses are intended to include those containing substantial deletions or mutations in their RNA.

The term "control region" refers to that region of a retrovirus that is duplicated after infection and prior to integration. Control regions include U3 and U5 regions. Such regions also include LTR regions.

The term "integration sequence" refers to any nucleic acid sequence which, when contacted with genomic DNA under appropriate conditions, causes the nucleic acid sequence or a portion thereof to fuse with the genomic DNA. Such integration sequences when used to introduce a protein coding sequence into genomic DNA result in a fusion involving no damage to the protein coding sequence and conservation of a portion of the integration sequence. Such integration sequences cause minimal damage to genomic DNA, except for interrupting the genomic sequence. Integration sequences include those known to occur in the control regions which are responsible for the integration of a retrovirus into genomic DNA. Integration sequences may be included in circularized nucleic acids or in linear nucleic acids.

The term "protein coding sequence" means a nucleotide sequence encoding a polypeptide chain which can be used to distinguish cells expressing the polypeptide chain from those not expressing the polypeptide chain. Protein coding sequences include those commonly referred to as selectable markers. Examples of protein coding sequences include those encoding a cell surface antigen and those encoding enzymes. A representative list of protein coding sequences includes thymidine kinase, beta-galactosidase, tryptophane synthetase, neomycine-phosphotransferase, histidinol-dehydrogenase, luciferase, cloramphenicol-acetyl transferase, dihydrofolate reductase (DHFR), hypoxanthine guanine phosphoribosyl transferase (HGPRT), CD4, CD8 and hygromycin-phosphotransferase (HYGRO).

The term "promoterless" refers to a protein coding sequence contained in a vector, retrovirus or provirus that is not under the control of a promoter within the vector, retrovirus or provirus. The vector, retrovirus or provirus may contain a promoter, but that promoter cannot be positioned or configured such that it regulates the expression of the promoterless protein coding sequence.

The term "assaying for the expression" of a protein coding sequence means any test or series of tests that permits cells expressing the protein to be distinguished from those that do not express the protein. Such tests include biochemical and biological tests.

The term "primer" refers to a nucleic acid which, when hybridized to a strand of DNA, is capable of initiating the synthesis of an extension product in the presence of a suitable polymerization agent. The primer preferably is sufficiently long to hybridize uniquely to a specific region of the DNA strand.

The term "PCR" refers to a procedure known as polymerase chain reaction which is described in U.S. Pat. No. 4,683,195, the disclosure of which is incorporated herein by reference.

The term "cell" as used herein means any eukaryotic cell. The cell may be a unicellular organism, part of a multicellular organism, or a fused or engineered cell in culture. The cell also may be part of an animal, and in one aspect of the invention is part of a transgenic animal.

The present invention involves the use of retroviruses as genetic tools to isolate transcriptionally active chromosomal regions. The novel retroviruses of the invention may be used to infect cells under conditions which permit selection for instances when the retrovirus integrates in close proximity to and under the control of a cellular promoter. The promoter (and its associated gene) then may be identified and isolated. In this manner, the retroviruses of the invention function as "promoter traps".

Figure 2:
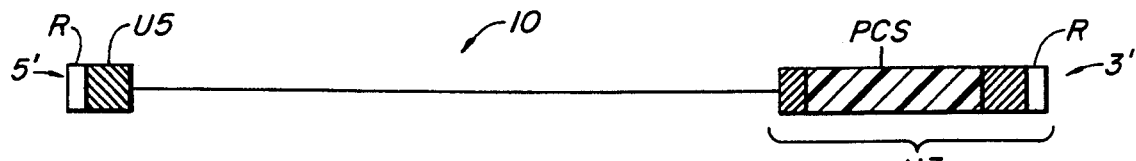
FIG. 2 is a schematic diagram of the genome of the retroviruses of the invention.

A preferred embodiment of the invention is shown in FIG. 2, which schematically illustrates a retrovirus which has been genetically manipulated to include in its control region a promoterless protein coding sequence. The retrovirus 10 is a segment of RNA having short sequence repeats R at its 5′ end and 3′ end. Just downstream of the short sequence repeat R at the 5′ end is a unique sequence U5. Just upstream of the short sequence repeat R at the 3′ end is a unique sequence U3. These sequences control DNA synthesis, integration, transcription and RNA processing.

Between the control regions are the coding sequences for the major structural proteins of the virus particle and for enzymes found in particles.

According to the invention, a protein coding sequence (PCS) has been inserted into the U3 sequence of the retrovirus. This protein coding sequence is promoterless with respect to the retrovirus. In the embodiment shown, the protein coding sequence is upstream of any promoter located in U3, and is close to the 5' end of U3. Preferably, the protein coding sequence is positioned as close as possible To the 5' end of U3. The protein coding sequence, however, should be downstream of the integration sequence in U3 which is located at the 5' end of U3.

Shortly after the retroviruses of the invention are used to infect cells, the vital RNA is converted into DNA by reverse transcriptase. Prior to integration into genomic DNA, the control regions of the virus are duplicated such that the retroviral genome is flanked by long terminal repeats (LTRs), each containing the U3, R and U5 sequences. The entire U3 region of the retrovirus of the invention is duplicated, including the protein coding sequence contained in U3.

Referring to FIG. 2, the provirus derived from the retrovirus of the invention is shown integrated into genomic DNA. The provirus 18 is flanked on either side by genomic DNA 20. The LTR at either end of the provirus contains U3 at the 5' end of the LTR and U5 at the 3' end of the LTR. The short sequence repeats R are sandwiched by U3 and U5 in each LTR. The promoterless protein coding sequence contained in the 5' LTR is positioned just downstream of flanking genomic DNA. In one preferred embodiment, the promoterless protein coding sequence was positioned just 30 nucleotides downstream of flanking genomic DNA.

The retroviruses of the invention have been used successfully to move promoterless protein coding sequences into genomic DNA. If an endogenous promoter is located in the genomic DNA nearby and upstream of the promoterless protein coding sequence, then the endogenous promoter may initiate the transcription of the protein coding sequence in the 5' LTR.

Cells containing a provirus integrated in a manner such that the promoterless protein coding sequence is under the control of an active endogenous promoter may be selected according to methods well known to those of ordinary skill in the art. The particular mode of selection will depend upon the particular protein coding sequence inserted into the U3. For example, cells may be selected based upon assays which select for the ability of the cells to grow in a certain medium. Cells also may be selected based upon the staining of an expressed protein or based upon an expressed enzyme that catalyzes a reaction. Cells also may be selected by various antibody techniques, including panning cells using a substrate coated with antibodies which recognize a cell surface protein encoded by the protein coding sequence, as for example CD4.

The foregoing methods are considered positive selection methods in that they select for instances wherein the endogenous promoter is active with respect to the protein coding sequence. Negative selection methods also may be employed. Negative selection methods involve removing cells which are actively expressing the protein coding sequence, by for example killing such cells, sorting them based on fluorescence or removing them by panning. The remaining cells then may be tested to determine whether proviruses have integrated next to promoters inactive at the time of the initial selection. Such cells may be treated with substances capable of activating a silent promoter, and then those cells expressing the protein coding sequence may be selected. Cell populations derived from negative selection thus are useful in identifying and isolating silent promoters. They are also useful in assay systems which test the ability of substances to influence the activity of promoters.

Once a clone of cells expressing the protein coding sequence has been selected, then the DNA flanking the provirus may be isolated. This may be accomplished by a variety of methods known to those of ordinary skill in the art, including any conventional method employing probes which hybridize to the provirus. Such methods typically involve breaking genomic DNA into smaller segments, for example by enzymatic cleavage, isolating from the DNA segments those containing at least a portion of the provirus using probes to the provirus, and then determining the sequence of the isolated segment.

In one particularly desirable procedure, PCR is employed to isolate the promoter and/or flanking DNA. This procedure is described in greater detail below, in connection with Example II. Briefly, genomic DNA including the provirus is cleaved to create small segments of DNA. Each of the segments then is circularized by ligation. Some of these circularized segments will include minimal a portion of the protein coding sequence and upstream flanking DNA. These segments are amplified by PCR using primers to the protein coding sequence. The amplified DNA then may be isolated and sequenced.

The retrovirus discussed above had a protein coding sequence inserted into its U3. The protein coding sequence also can be inserted into U5. However, the protein coding sequence in a U5 should be oriented transcriptionally in the 3'–5' direction, and it may be necessary to add a polyadenylation sequence as will be recognized by one of ordinary skill in the art. A protein coding sequence in U5 must be promoterless with respect to the provirus and must be between integration sequences.

It will be apparent to those of ordinary skill in the art that synthetic molecules may be used in constructing recombinant promoter traps. Such molecules would include a promoterless protein coding sequence flanked by synthetic integration sequences. Such provirus-like molecules then may be introduced into cells and may integrate into genomic DNA in a manner such that the promoterless protein coding sequence is under the transcriptional control of an endogenous promoter.

The retroviruses of the invention have many uses. As described above, they may be used to identify and isolate promoters and associated genes. They also may be used as insertional mutagens to study gene function and gene development. They further may be used to induce germ line mutations and to create transgenic animals with such mutations.

The cells of the invention contain the proviruses and retroviruses of the invention. The cells of course may be used in connection with identifying and isolating promoters and their associated genes. The cells may be used in connection with studying gene function and development. They also may be used in assay systems for screening drugs, including drugs affecting the expression of genes and drugs that inhibit oncogene functions. Cells containing the proviruses of the invention further may be used as producer lines for the retroviruses of the invention. Some examples of the methods and products of the invention are as follows:

INSERTIONAL MUTAGENESIS

Promoter-trap retroviruses allow genes responsible for a variety of cellular functions to be isolated. The general scheme involves: (i) infecting cells with promoter trap retroviruses such as U3His, (ii) selecting for a large (10–100,000) collection of histidinol-resistant clones (these clones, referred to as an integration library, collectively contain proviruses inserted into all genes with promoters capable of expressing his at levels sufficient to confer resistance), (iii) screening the integration library for clones which fail to express some gene function (iv) determining whether the gene displaced by the promoter trap vector is displaced in other clones where the gene function was lost. For example, the integration library may be sorted by using an antibody in conjunction with the fluorescence activated cell sorter or antibody panning for clones which fail to express a specific cell surface protein. Independent clones selected in this manner can be analyzed for the site of provirus integration, by testing (southern blot hybridization) whether flanking sequences are linked to the provirus in other non-expressing clones. If multiple integrations have occurred at the same site, then the gene encoding the cell surface protein can be cloned as cellular sequences linked to his.

DEVELOPMENT OF DRUG ASSAYS TO SCREEN FOR INHIBITORS OF ONCOGENE FUNCTIONS

This method involves isolating cell clones in which reporter genes transduced by the retrovirus have fused to promoters that are regulated by an oncogene. The general scheme involves: (i) infecting cells with promoter trap gretroviruses such as U3CD4 which carries coding sequences for CD4, a gene which allows selection both for and against transcriptional activation of proviral genes by flanking cellular promoters and a neomycin resistance gene which allows provirus-containing cells to be isolated whether or not they express CD4, (ii) isolating an integration library of clones which express CD4 (iii), introducing an activated oncogene such as ras by DNA mediated gene transfer or by retrovirus transduction into cells of the integration library and (iv) isolating cells which fail to express CD4. At least some of these clones fail to express CD4 because the promoter which originally activated CD4 expression is repressed by ras. Such cell lines can be used to isolate agents which inhibit ras or signaling pathways distal to ras by screening for the reactivation of CD4 expression. This type of assay is relatively specific in that compounds which kill cells or inhibit macromolecular synthesis will not score positively. Similarly, introducing ras into a library of clones which fail to express CD4 (isolated by treating neomycin resistant cells with anti-CD4 antibody and complement) and selecting for CD4 expression will yield cell lines in which the retrovirus had inserted next to promoters that are induced by ras. Clones of this type can be used to isolate agents that inhibit ras based on their ability to inhibit CD4 expression.

USE OF PROMOTER TRAP RETROVIRUS VECTORS TO INDUCE GERM LINE MUTATIONS IN MICE

Retrovirus promoter trap vectors will enable mice strains deficient in different functions to be isolated. The method involves (i) infecting murine embryohal stem (ES) cells with the promoter traps of this invention (ii) isolating ES cell clones that have integrated protein coding sequences regulated by endogenous promoters—for example, by selecting histidinol resistant cells following infection with a retrovirus containing histidinol dehydrogenase in U3 (U3 His virus) (iii) transferring selected ES cells into blastocysts, and (iv) breeding of chimeric offspring to obtain transgenic mice which carry germline integrations of the U3His virus. Mice containing germ line integrations of the U3 His virus may be bred to homozygosity. Phenotypes resulting from gene inactivation due to U3 His virus integration may be identified.

USE OF PROMOTER TRAP VECTORS TO STUDY GENE EXPRESSION DURING DEVELOPMENT

A retrovirus containing a reporter gene such as lacZ inserted into U3 is advantageous for this purpose since the product of the lacZ gene ($\beta$-galactosidase) is readily detected by histochemical staining. ES cells may be infected with the U3/lacZ vector and stem cell clones which express lacZ may be isolated. Transgenic mice derived from those clones may then be used to study temporal and spatial expression of $\beta$-galactosidase during embryological development.

EXAMPLE I

A retrovirus containing histidinol dehydrogenase in U3 was constructed and used as a promoter trap to identify endogenous promoters.

Viruses And Cells

GgU3Hisen(−) and GgTKNeoU3Hisen(−) viruses were constructed from GgTKNeoen(−), a recombinant Moloney murine leukemia virus (P. Robbins and R. Mulligan, M. I. T., Cambridge, Massachusetts). GgTKNeoen(−) was derived from pHSG-neo [1] and contained sequences extending from the 5′ LTR to the Xho I site at nucleotide (nt.)1558, a bacterial neomycin phosphotransferase gene (NEO) expressed from the HSV thymidine kinase (TK) promoter [2], provital sequences extending from the Cla I site (nt. 7672) through the 3′ LTR, and lacks sequences between the PvU II and XbaI sites (nt. 7933–8111) that contain the viral transcriptional enhancer. Coding sequences for the Salmonella typhimurium HIS-D gene, isolated from pSP1 (B. Handelin and D. Housman, MIT, Cambridge, Mass.) as a 1350 nt. BamH I fragment, were ligated to the Nhe I site (nt. 7846) in U3 of GgTKNeoen(−) to obtain GgTKNeoU3Hisen(−). GgU3Hisen(−) was derived from GgTKNeoU3Hisen(−) by deleting the BamH I fragment containing TKNeo.

Cells were grown in Dulbecco's Modified Egles medium supplemented with 10% calf 'serum (NIH 3T3 and Ψ2 [4]) or 10% fetal calf serum (PA317 [5]). Cell lines producing recombinant retroviruses were derived after transfecting [6]Ψ2 or PA317 cells with plasmid DNAs and selecting in medium containing G418 (1 mg/ml., Gibco/BRL, Gaithesberg, Md.). After ten days, G418 resistant colonies were isolated and expanded in mass culture.

To prepare virus stocks, $2 \times 10^6$ cells from each clone were seeded into 100 mm dishes. The following day, 2 ml of fresh medium was added, and after two hours the medium was filtered through a 0.22 μm Millipore membrane (Millipore, Bedford, Ma.) and stored at −70° C. until use. One ml of different dilutions of virus stocks was added to $1 \times 10^5$ NIH 3T3 cells plated one day before infection. Following incubation for one hour at 37° C. in the presence of 8 mg/ml polybrene (Aldrich, Milwaukee, WI.), 9 ml of fresh medium was added. After incubating overnight cells were grown for 10 days in selective medium containing 1 mg/ml G418 or 4 mM L-histidinol (Sigma, St. Louis, MO.). Colonies were fixed (10% (v/v) formaldehyde in PBS) and stained with crystal violet prior to counting.

Southern Hybridization Analysis

Genomic DNA, extracted from His-resistant ($HIS^r$) or Neo-resistant ($NEO^r$) NIH 3T3 lines, was digested to completion with restriction endonucleases Cla I,. Cla I and Sal I or Hind III, fractionated in 1% (w/v) agarose gels, and transferred to nylon membranes (Zetabind; Cuno, Meridian, Ct.) as described [7]. Blots were hybridized to $^{32}P$-labeled probes prepared from the 1.35 kb HIS coding sequence by The random priming method [8].

Northern Hybridization Analysis

Total cellular RNA was extracted form $HIS^r$ or $NEO^r$ NIH 3T3 cell lines using the guanidinium thiocyanate procedure. RNA was fractionated on formaldehyde/agarose gels and transferred to nylon membranes (Gene-Screen-Plus, New England Nuclear, Boston, Ma.) by electroblotting in 25 mM phosphate buffer. DNA-RNA hybridizations were carried out as previously described [9] using $^{32}P$-labeled restriction fragments corresponding to HIS (1.35 Kb Nhe I; GgU3-Hisen(−)), NEO (1.2 Kb Bgl II/BamH I; GgTKneo-en(−)) and gag (1.1Kb Pvu I//Xho I; GgU3Hisen(−)) sequences.

Ribonuclease Protection Assays

20 μg of cellular RNA was hybridized at 55° C. for 10 hours to $^{32}P$-labeled RNA probes ($4 \times 10^5$ cpm) in 30 ml of 80% (v/v) formamide, 0.4M NaCl, 0.04M PIPES (pH 6) (Sigma) and 0.001M EDTA. Probes complementary to the proviral coding strand were prepared using T3 RNA polymerase (Promega-Biotec, Madison, WI) to transcribe a 860 nucleotide BamHI/ClaI fragment of GgTKNeoU3Hisen(−) cloned into Bluescript KS(+) (Stratagene, La Jolla, Ca.). Following hybridization, samples were digested with ribonucleases A (Boehringer-Mannheim, Indianapolis, In.), and T1 (GIBCO/BRL) and processed for gel electrophoresis according to the instructions supplied by Promega Biotec. Protected fragments were separated on denaturing 6% polyacrylamide-8.3M urea gels and visualized by autoradiography.

Results

Figure 4:
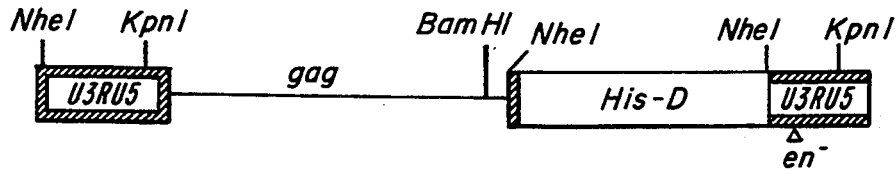
FIG. 4 is a schematic diagram of the genome of The retrovirus of GgU3Hisen(−)
Figure 5:
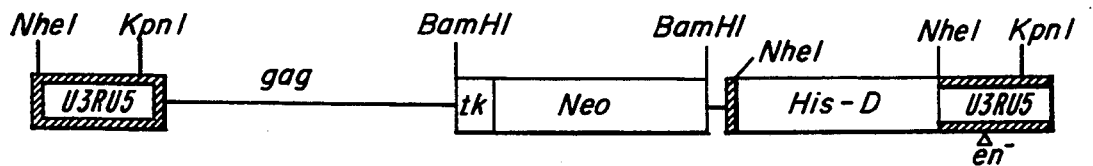
FIG. 5 is a schematic diagram of the genome of the retrovirus GgTKNeoU3Hisen(−)

The Retroviruses GgU3Hisen(−) (FIG. 4) and GgTKNeoU3Hisen(−) (FIG. 5) were constructed from a Moloney Murine Leukemia provirus (P. Robbins and R. Mulligan, M. I. T., Cambridge, Ma.), by inserting the histidinol dehydrogenase (His-D) coding sequence from Salmonella typhimurium ([10]) into the U3 region of the 3′ LTR and by deleting enhancer sequences of the LTR. The designation en(−) denotes a 178-nt. deletion in the 3′ LTR encompassing the viral enhancer. The designation gag denotes the truncated gag region of MoMuLV. GgTKNeoU3Hisen(−) also contains a neomycin-resistance gene (neomycin phosphotransferase) under the transcriptional control of the herpes simplex virus (HSV) thymidine kinase (TK) promoter to provide an independent measure of virus titers.

Virus producing cell lines were generated by transfecting GgTKNeoU3Hisen(−) into NIH3T3 cells expressing packaging-defective ecotropic (Ψ2) and amphotropic (PA317) helper viruses. Viruses recovered from cloned producer lines were titered on NIH 3T3 cells, selecting in either G418 (Geneticin, an animoglycoside antibiotic available from GIBCO/BRL) or L-histidinol. Titers of the GgTKNeoU3Hisen(−) virus were similar to what we and others have obtained with other MoMLV vectors, suggesting that the insertion of HIS sequences into the LTR did not markedly interfere with virus replication or integration. As is generally observed, ecotropic Ψ2 cells produced higher yields of virus than amphotropic PA317 cells; however, the ratio of HIS to NEO colony forming units was similar for each virus stock, about $3.8 \times 10^4$.

Figure 6:
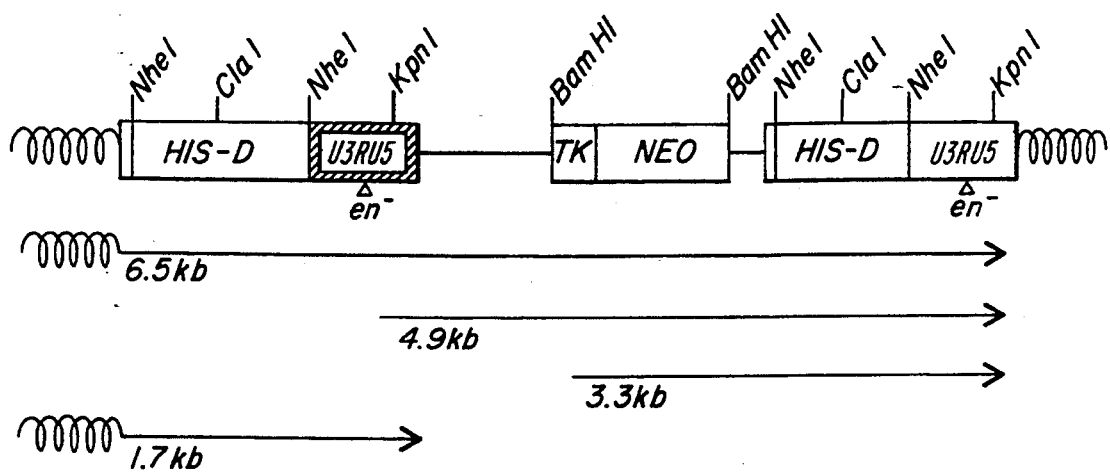
FIG. 6 is a schematic diagram of the genome of the provirus GgTKNeoU3Hisen(−) analyzed by Southern blot hybridization with transcripts identified by northern blot hybridization.

The structure of the integrated GgTKNeoU3-Hisen(−) proviruses in 6 independent NEO—and HIS—resistant clones was analyzed by Southern blot hybridization (FIG. 6). Cell DNAs (approximately 10 μg per lane) digested with Cla I, Cla I and Sal I and Hind III were fractionated on agarose gels, blotted to nylon filters, and hybridized to HIS probes.

Regardless of the initial selection, all but one clone contained proviruses in which HIS sequences had duplicated as part of the LTR. Thus, Cla I and Sal I endonucleases generated fragments expected from proviruses flanked by LTRs containing HIS. Cleavage fragments of 4.9 kb or 4 kb and 0.9 kb were generated following digestion with Cla I alone or together with Sal I, respectively. Only the Neo-selected ΨC7 line lacked the expected proviral fragments; however, this line lacked most if not all HIS sequences and expressed aberrant NEO transcripts, suggesting that the proviral DNA had rearranged. Additional bands of varying sizes represent fragments that extend from Cla I sites in the provirus to sites in the flanking cellular DNA.

To estimate the number of proviruses per cell, cellular DNAs were digested with Hind III or Nde I, enzymes that do not cut within the provirus. All clones contained from i-3 proviruses, and in all cases, hybridization patterns were unique, confirming that each line was an independent clone.

Relatively Few Proviruses Acquire the Ability to Express HIS

The ratio of NEO and HIS titers indicates that provirus integration was 2500 fold less likely to convert cells to a HIS resistant phenotype than to a NEO resistant phenotype. In principle, the potential to express HIS resistance could be an intrinsic, but inefficient, property of each provirus. For example, translation of 3′ HIS sequences in transcripts initiated at the TK promoter could allow some HIS expression. Alternatively, HIS expression may require secondary events, such as mutations or transcriptional activation by adjacent cellular sequences. Several experiments suggest that the capacity to transduce HIS resistance is not an intrinsic property of the infecting virus. Cells initially selected in G418 did not survive when transferred to media containing L-histidinol., indicating that most proviruses did not confer HIS resistance. In addition, the number of doubly resistant colonies produced after plating GgTKNeoU3Hisen(−) infected cells in medium containing both G418 and L-histidinol was similar (within a factor of two) to the number of colonies obtained following selection in L-histidinol alone. This implies that only a subset of the proviruses conferring NEO resistance was capable of expressing HIS resistance. Finally, the ability to passage HIS resistance did not require the TK promoter, since HIS titers for the GgTKNeoU3-Hisen(−) and GgU3Hisen(−) viruses were nearly identical Although secondary events apparently influence the ability of U3HIS vectors to transduce HIS, several experiments suggest HIS expression is not activated by mutations within the provirus. First, the proviruses in $HIS^r$ clones lacked gross sequence rearrangements as judged by Southern blot analysis. Second, proviruses rescued from $HIS^r$ clones following superinfection with wild type MoMLV did not transduce HIS any more efficiently (as compared to NEO) than the original U3His vector.

HIS Transcripts Initiate in the Flanking Cellular DNA

HIS TRANSCRIPTS INITIATE IN THE FLANKING CELLULAR DNA

To further examine why only certain proviruses expressed HIS, transcription of proviral sequences in $HIS^r$ and $NEO^r$ clones was analyzed by Northern blot hybridization Total cellular RNA (10 micrograms per lane) was extracted from $NEO^r$ and $HIS^r$ clones, fractionated on formaldehyde-agarose gels, transferred to nylon membranes and hybridized to HIS or NEO specific probes. All lines, whether selected in G418 or L-histidinol, expressed 4.9 and 3.3 kb proviral transcripts, while lines selected in L-histidinol expressed two additional transcripts of 6.5 and 1.7 Kb. These RNAs were mapped according to their ability to hybridize to HIS—, NEO—and gag-specific probes. Briefly, all four transcripts hybridized to HIS; the 6.5 and 4.9 and 3.3 kb RNAs hybridized to NEO; and only the 6.5 and 4.9 kb species hybridized to gag. These data suggest that the 4.9 and 3.3 RNAs start at the 5' LTR and at the TK promoter, respectively, and terminate in the 3' LTR; whereas, the 6.5 and 1.7 kb RNAs in $HIS^r$ clones appear to initiate outside the provirus and terminate at polyadenylation sites in the 3' and 5' LTRs, respectively.

The sizes of the smaller (1.7 kb) transcripts in HIS clones were never quite the same but varied by as much as 100 base pairs. This is the result one might expect if the proviruses were located at different distances from cellular promoters, and the size of each transcript depended on the amount of appended cellular RNA. In most cases, cell-derived sequences are expected to be short, since efficient translation of native histidinol dehydrogenase requires that the first AUG in the hybrid transcript be the initiating codon for histidinol dehydrogenase. For the average mammalian gene, these sequences would average 50–100 nucleotides. While transcription probably starts in sequences immediately adjacent to the provirus, these results do not exclude the possibility that integration has occurred 3' to a splice acceptor site.

Figure 7:
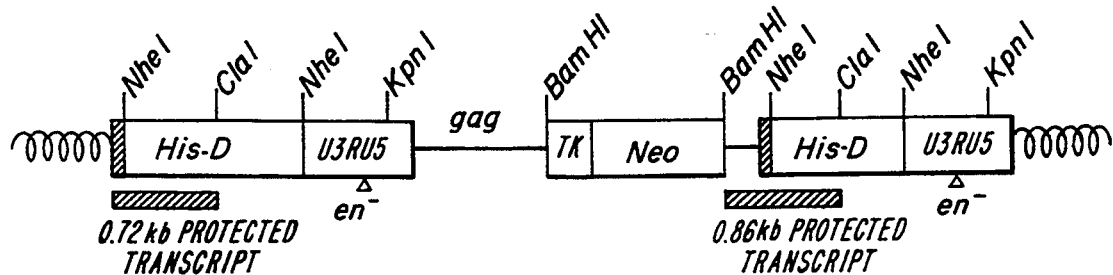
FIG. 7 is a schematic diagram of the genome of the provirus GgTKNeoU3Hisen(−) analyzed by Protection assays.

To confirm that transcripts in histidinol-selected clones initiated within the flanking cellular DNA, total RNA was extracted and analyzed using a ribonuclease protection assay as shown in FIG. 7. $^{32}$P-labeled RNA probes, complementary to the proviral coding strand, extending from the Cla I and BamH I sites in GgTKNeoU3Hisen(−), were prepared using T3 RNA polymerase. RNA extracted from virus-producing lines or from HIS and NEO-selected lines protected a 860 bp fragment. This corresponds to transcripts colinear with the proviral template, including both MoMLV and HIS sequences. However, RNA from HIS-resistant lines generated an additional fragment of 720 bp., exactly the size expected for transcripts colinear with proviral sequences extending from the Cla I site to the 5' end of the LTR.

EXAMPLE II

In this example, polymerase chain reaction (11) was used to isolate sequences upstream of U3HIS proviruses. Probes to upstream sequences protected transcripts expressed in uninfected cells, indicating that upstream promoters were transcriptionally active prior to virus integration. Moreover, 2 out of 4 transcribed flanking sequences cloned promoted high levels of expression of a chloramphenicol-acetyl-transferase (CAT) reporter gene.

Cell cultures $HIS^r$ cell lines, isolated as previously described in Example I, were grown in Dulbecco's modified Eagle's Medium (Gibco) supplemented with 10% calf serum.

Amplification and sequencing of proviral flanking sequences

Genomic DNAs from $HIS^r$ cell lines were digested with HinfI and ligated at a concentration of 5 μg/ml to obtain circular molecules. After cleaving with PvuII, 1 μg of DNA from each sample was used for the polymerase chain reaction (PCR). PCRs were performed in 100 ml of 10 mM TRIS, pH 8.3, 5 mM KCl, 1.5 mMMg2Cl, 200 mM of each desoxyribonucleotide triphosphate, 2.5 U AmplitaqR polymerase (Perkin-Elmer Cetus) and 1 mM of each primer (5'-CCAGT-CAATCAGGGTATTGA-3', and 5'-GTCAGC-GATATTCTGGATA-3'). Reactions proceeded through 40 cycles of denaturation (95° C. for 1.5 min) primer annealing (50° C. for 1.5 min), and primer extension (72° C. for 3 min). Gel purified PCR products were cleaved with NheI and SspI, and ligated to Bluescript KS(.-) (Stratagene) plasmids digested with XbaI and EcoRV.

Nucleotide sequences of provirus-cell DNA junctions were determined by the dideoxy chain termination method as described (12).

Ribonuclease Protection Assays

Cellular RNA (30 μg) was hybridized at 50° C. for 10 hours to $^{32}$P-labeled RNA probes (4×10$^5$ cpm) in 30 ml of 80% (v/v) formamide, 0.4M NaCl, 0.04 M PIPES (pH 6) (Sigma) and 0.001M EDTA. Probes complementary to the provirus flanking region coding strands extending through the U3 junction to a BssHII restriction site 66 nt downstream of the junction were prepared by using T7 RNA polymerase (Promega Biotec) to transcribe the NheI/BssHII fragments cloned into pBluescript KS(−). After hybridization, samples were digested with RNAses A (Boehringer-Mannheim) and T1

(GIBCO/BRL) at concentrations of 5 μp/ml and 1000 U/ml, respectively. Protected fragments were separated on denaturing 8% polyacrylamide-8.3 M urea gels and visualized by autoradiography.

Analysis Of Promoter Activity

To estimate the ability of flanking sequences to activate the expression of a linked reporter gene, fragments containing provirus-cell DNA junctions (isolated after digesting pBluescript clones with NotI and HindIII) were ligated to pCAT (digested with BglII and HindIII). Prior to ligation, NotI and BglII ends were made blunt using Klenow polymerase. pCAT was derived from pTKCAT (13) by removing the TK promoter sequences. 20 μg of each pCAT plasmid together with 20 μg pCH110 (Pharmacia)(14), a reporter plasmid expressing β-galactosidase, were co-transfected into NIH3T3 cells as previously described (15). After incubating for 48 hours, cells were recovered in 100 ml of 0.25 mM TRIS, pH 8 and lysed by freeze-thawing. Chloramphenicol acetyl transferase assays were performed in liquid scintillation vials containing 250 μl of 100 mM TRIS, pH 8, 1 mM Chloramphenicol (Sigma) and 1 μCi $^3$H-acetyl CoA (New England Nuclear NET-290L, 200 mCi/mmol). Samples were overlaid with 3 ml of water-immiscible scintillation flour (Econofluor, DuPont) (16) and incubated for 3 hours at room temperature. Production of $^3$H-acetyl chloramphenicol, proportional to the amount of radioactivity released into the organic phase, was measured by liquid scintillation. CAT activity, expressed as CPM per milligram of cell protein (determined by the Bradford method (17)), was normalized for β-galactosidase expression to control for variation in transfection efficiencies. For this 35 ml of cell extracts were mixed with 1 ml of Z buffer (18) containing 30 mmoles/L 2-mercaptoethanol (Sigma) and 0.8 mg/ml α-nitrophenyl-β-galactosidase (Sigma) and the absorbance at 420 nm was determined after incubating 30 min at room temperature (19).

RESULTS

Three out of four HIS$^r$ cell lines examined in the present study contained 2 proviruses, reflecting the initial multiplicity of infection. To isolate cellular sequences that might have activated HIS expression, DNA flanking the 5'end of U3HIS proviruses was amplified by the polymerase chain reaction (PCR). In general PCR requires two oligonucleotide primers complementary to sequences on each strand and at opposite ends of the DNA fragment to be amplified. Although the genomic sequences upstream of U3HIS proviruses are flanked only on one side by a known sequence (i.e. the provirus), it was possible to link both ends of the flanking cellular DNA to the provirus by (i) digesting cellular DNA with a restriction endonuclease that generates fragments small enough to be amplified, and (ii) ligating the DNA to obtain circular molecules where both ends of the cellular DNA are linked to provirus sequences (20).

Figure 8:
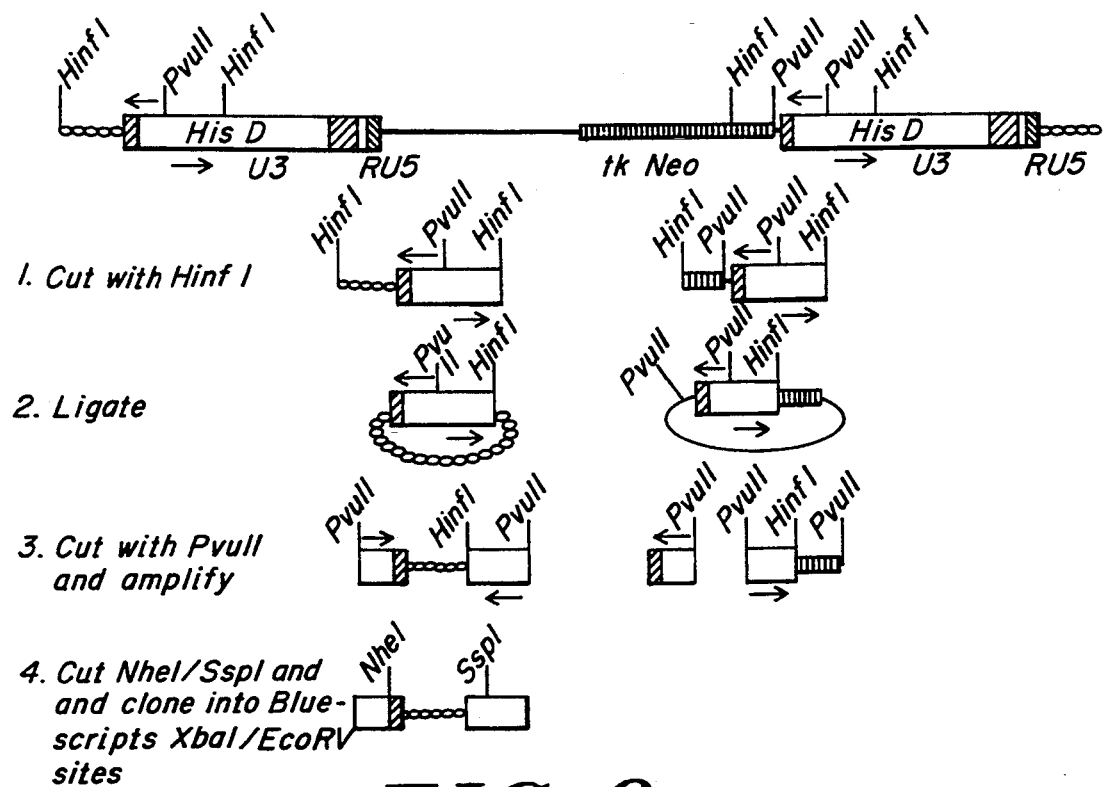
FIG. 8 is a schematic diagram of PCR amplification of the genomic DNA flanking the 5′ end of the provirus of FIG. 7.

Oligonucleotides were synthesized that would prime polymerase reactions in opposite directions from a PvuII site located 72 nucleotides from the end of the LTR (FIG. 8). To generate small restriction fragments that amplify more efficiently, genomic DNA was digested to completion with HinfI, yielding an average fragment length of 800 nt. HinfI fragments were circularized using DNA ligase, thus positioning 5' flanking sequences between the proviral priming sites. To avoid PCR products originating from circles formed at the 3'end of the provirus, the DNA was digested with PvuII which cleaves fragments derived from the 3'LTR (FIG. 8). Such separation was less likely to occur at the left end because PvuII sites are an order of magnitude less frequent than HinfI sites in mammalian DNA.

PCR products from each HIS$^r$ line varied in size as one might expect if flanking HinfI sites were located at different distances from the proviruses. Accordingly, amplified fragments ranged 725–1130 nt in size which corresponds to 95–500 nt of cellular DNA appended to a 630 nt U3his segment. In some clones, digestion by PvuII was incomplete resulting in a PCR product of 680 nt, derived from the 3'end of the provirus. With the exception of Ψ9 cells, the number of amplification products matched the number of integrated proviruses, indicating that in most instances it was possible to amplify upstream cellular sequences. However, this strategy is not expected to amplify upstream sequences in cases where the HinfI sites are far apart or when the flanking fragment is cleaved by PvuII.

Amplified DNAs were digested with NheI/SspI and cloned into plasmid vectors digested with XbaI and EcoRV. Sequence analysis of the cloned PCR products confirmed that each contained authentic junctions between viral and cellular DNA (FIG. 9). Each junction lacked the last 2 nt of U3 normally deleted during provirus integration (44) thus, HIS sequences did not interfere with recognition or ligation of sequences near the end of U3. U3 sequences were otherwise unaltered, except one provirus in ω7 cells contained a 4 nt substitution in the inverted repeat region (boxed region, FIG. 9). This alteration was not a PCR artifact, since the same sequence was found in a fragment isolated from an independent amplification reaction. However, the mutation may have occurred following provirus integration, since similar mutations in U5 seriously affect viral replication (21).

Figure 3:
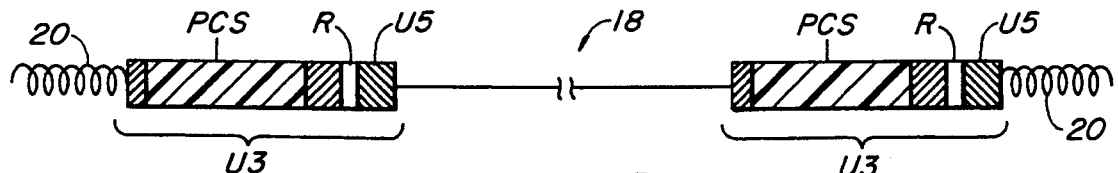
FIG. 3 is a schematic diagram of a provirus of the invention integrated into genomic DNA.

The cellular portion of each sequence was unique, (FIG. 9) indicating that each provirus was derived from an independent integration event. Computer analysis of the flanking sequences failed to identify similar sequences in the Genbank and EMBL databases, except for the ω7b flanking sequence (FIG. 3) which was 84% identical to the consensus sequence (nt 89-38) of a B1 repetitive element (22, 23).

Figure 10:
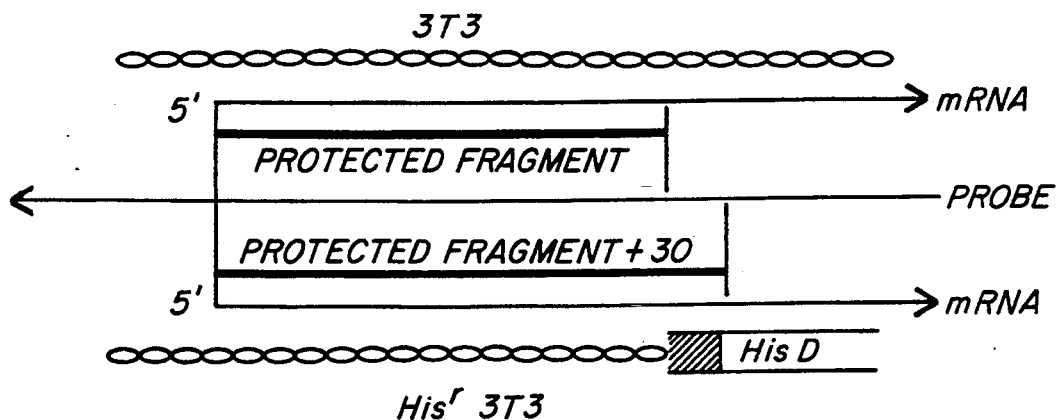
FIG. 10 is a schematic diagram of a Protection assay.

Sequences flanking U3His proviruses are complementary to cellular transcripts and contain active promoters. If flanking promoters were active prior to proviral integration, then sequences flanking the provirus should be expressed on cellular transcripts isolated from uninfected cells. $^{32}$P-labeled RNA probes complementary to provirus-flanking sequences were prepared and hybridized to RNA extracted from 3T3 cells. RNA probes from each clone examined protected transcripts in 3T3 cells. However, such transcripts were detected only by one of the two probes isolated from cell lines with two proviruses, indicating that only one provirus had integrated into an expressed site. Protected fragments varied in size as one might expect from transcripts initiated in different genes. When hybridized to RNA from corresponding parental lines, two probes (P3a, Ψ7b) protected additional fragments that were 30 nt larger than the largest fragments protected by 3T3 RNA, exactly the size expected for transcripts initiated in the allele containing the provirus (FIG. 10).

Although flanking probes P7 and Ψ9 hybridized to RNA from 3T3 cells, transcripts containing virus-cell junctions were not detected in P7 and Ψ9 cells. The reasons for this are not known. Short probes complementary to LTRHIS sequences failed to detect a splice site that could have deleted 5'U3 sequences. Instead, RNA from all HIS$^r$ clones examined, protected fragments of the exact size expected for cellular transcripts extending through the 5'end of the provirus. It is possible that mutations introduced during PCR prevented allergic transcripts from being detected.

Figure 11:
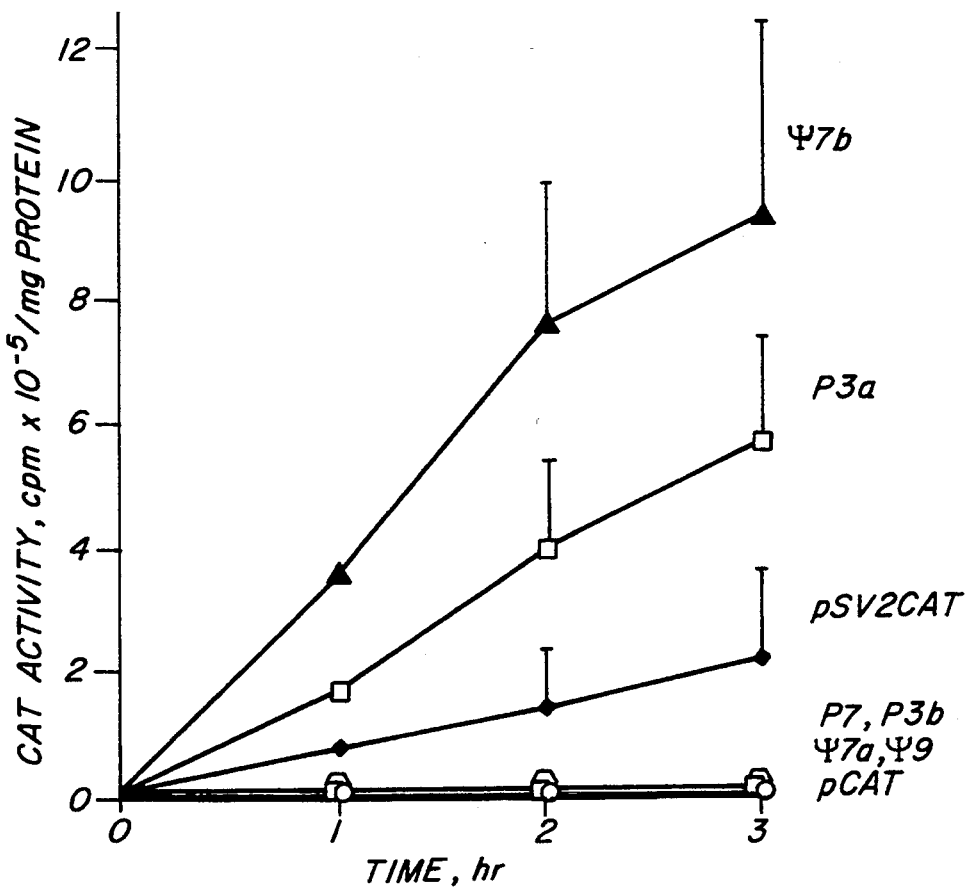
FIG. 11 is a graph showing promoter activity of isolated genomic DNA flanking provital integrants.

Finally, to investigate the ability of transcribed flanking sequences to activate expression of a linked reporter gene, provirus-cell DNA junctions were cloned into pCAT expression vectors and transfected into NIH3T3 cells. When tested for their ability to activate the expression the chloramphenicol-acetyl transferase gene in transient transfection assays, two flanking sequences stimulated CAT expression at a level greater than the SV40 early region promoter (FIG. 11).

EXAMPLE III

While the U3HIS virus tags promoters which are active at the time of histidinol selection, the vector is not well suited for identifying regulated promoters. For this reason, we have investigated the properties of a promoter-trap vector (U3LacZ) containing the E. coli lacZ gene inserted in U3. An advantage of using lacZ as a reporter of gene fusions is that β-galactosidase expression is readily monitored by enzymatic assays and by histological staining. Furthermore viable cells expressing β-galactosidase can be isolated by using the fluorescence activated cell sorter (FACS) [45]. The U3LacZ virus also contains a neomycin-resistance gene expressed from an internal promoter. The NEOgene provides an independent measure of virus titers and allows provirus containing clones to be isolated whether or not they express β-galactosidase.

The U3LacZ virus functions as a promoter trap in a manner similar to U3His. While the U3LacZ vector contains the longest reported LTR (3.4 kb), lacZ sequences did not interfere with the ability of the virus to transduce neomycin resistance. Cell clones expressing β-galactosidase were isolated by FACS and invariably contained proviruses in which transcription of the 5' copy of lacZ was activated by upstream cellular promoters. The U3LacZ vector can be used to isolate regulated promoters and to study temporal and spatial patterns of gene expression, in vivo.

Plasmids.

pGgTKNeoU3LacZen(−) was derived from pGgTKneoU3His (Example I) by replacing the hisD gene with E. coli lacZ coding sequences obtained as a 3.1 kb HindIII-XbaI fragment from pSDKLacZ (obtained from Pharmacia, Uppsala, Sweden). pSDKLacZ contains a lacZ gene with upstream Shine Dalgarno (24) (25) and Kozak (26) consensus sequences.

Cells and viruses.

Cell lines expressing packaging defective ecotropic (Ψ2) (27) and amphotropic (PA317) (28) helper viruses were transfected with 10 mg of pGgTKNeoLacZen(−) and selected in G418. Preparation of virus stocks and infection of NIH3T3 cells was carried out as previously described (in Example I).

Analysis of β-galactosidase activity.

β-galactosidase expression was monitored by staining U3LacZ infected NIH3T3 cells with 5-bromo-4-chloro-3-indolyl-β-D-galactopyranoside (X-Gal) and scoring the number of blue cells after 4 hours as previously described. β-galactosidase activity was quantitated as described by Norton (30) by using o-Nitrophenyl β-D-galactosidase (ONPG) as a substrate. For FACS analysis, NIH3T3 cells were treated with fluorescein di-β-D-galactopyranoside (FDG) (Molecular Probes, Eugene, Or.) (31) and sorted according to fluorescence intensity into LacZ+ and LacZ- using a Becton Dickinson (Franklin Lake, N.J.) FACS star plus cell sorter with a 530-nm band-pass filter

Southern hybridization analysis.

Genomic DNA extracted from LacZ+ and LacZ-NIH3T3 cell lines was digested to completion with ClaI, EcoRI or HindIII, fractionated in 1% (w/v) agarose gels and transferred to Nitroplus 2000 hybridization membranes (Micron Separations Inc., Westboro, Ma.) as previously described (32). Blots were hybridized to $^{32}$P-labeled restriction endonuclease fragments prepared from the 3 kbp BamHI-EcoRI fragment containing the LacZ coding sequence by the random priming method (33).

Northern hybridization analysis.

Total cellular RNA was extracted from LacZ + and LacZ−NIH3T3 cells by the guanidinium thiocyanate procedure. Polyadenylated RNA (poly A+) was obtained by using a mRNA purification kit (Pharmacia-)and the manufacturers instructions. The RNA was fractionated on 1% formaldehyde-agarose gels, transferred to Nitroplus 2000 hybridization membranes (Micron Separations Inc.) and hybridized to $^{32}$P-labeled probes as previously described [32]. Labelled restriction fragments corresponded to lacZ (3 kb BamHI-EcoRI fragment); neo(1.2 kb BglII-BamHI fragment) and gag (1.1 kb PvuI-XhoI fragment) of pGgTKNeoU3LacZen(−).

RNAase protection assay.

Cellular RNA (30 μg) was hybridized at 55° C. for 12 hr to P-labeled probes as previously described (35, 36). Probes complementary to the provirus coding strand were prepared by using T3 RNA polymerase to transcribe a 228 nt BamHI-NruI fragment of pGgTKNeoLacZen(−) cloned into Bluescript KS(−) (Stratagene). After hybridization, samples were digested with 5 μg/ml of RNAase A and 2 μg/ml of T1 (Boehringer Mannhelm Biochemicals), processed for gel electrophoresis as previously described (35, 36). Protected fragments were separated on denaturing 6% polyacrylamide-8.3M urea gels and visualized by autoradiography.

RESULTS

LacZ sequences in U3 do not interfere with virus infectivity.

Figure 12:
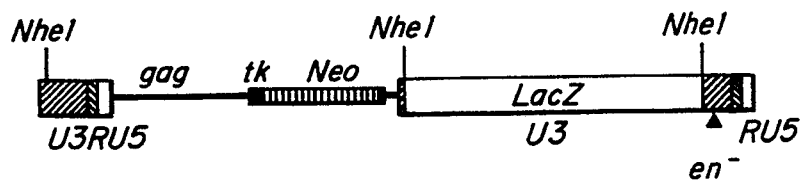
FIG. 12 is a schematic diagram of the genome of retrovirus PGgTKNeoU3LacZen(−)

The structure of the pGqTKNeoU3LacZen(-1) is shown in FIG. 12. Like GgTKNeoU3Hisen(−), pGgTKNeoU3LacZen(−) also contains a neogene under the transcriptional control of the HSV-2 thymidine kinase promoter to provide an independent measure of virus titers.

Cell lines producing ecotropic and amphotropic U3-LacZ viruses were generated by transfecting 10 mg of pGgTKNeoU3LacZen(−) into Ψ2 (27) and PAC317 (28) lines respectively. Virus recovered from cloned producer lines were titrated on NIH3T3 cells by selecting in G418. Titers of the U3LacZ virus were high and similar to those obtained with the U3His viruses of Example I. This suggests that the 3.1 Kbp lacZ extra sequence inserted into the LTR did not impair the ability of the virus to be passaged into recipient cells.

Most U3LacZ proviruses do not express β-galactosidase. NIH3T3 cells were infected at an M. O. I. of 1 NEO$^r$ CFU/cell and lacZ expression was monitored by staining with the chromogenic substrate, X-Gal. Approximately 0.6% of the NEO$^r$colonies expressed detectable β-gal and stained blue with X-Gal whereas NEO$^r$ colonies isolated after infection with control (U3His) virus failed to stain.

Enrichment of β-galactosidase expressing clones.

Figure 13:
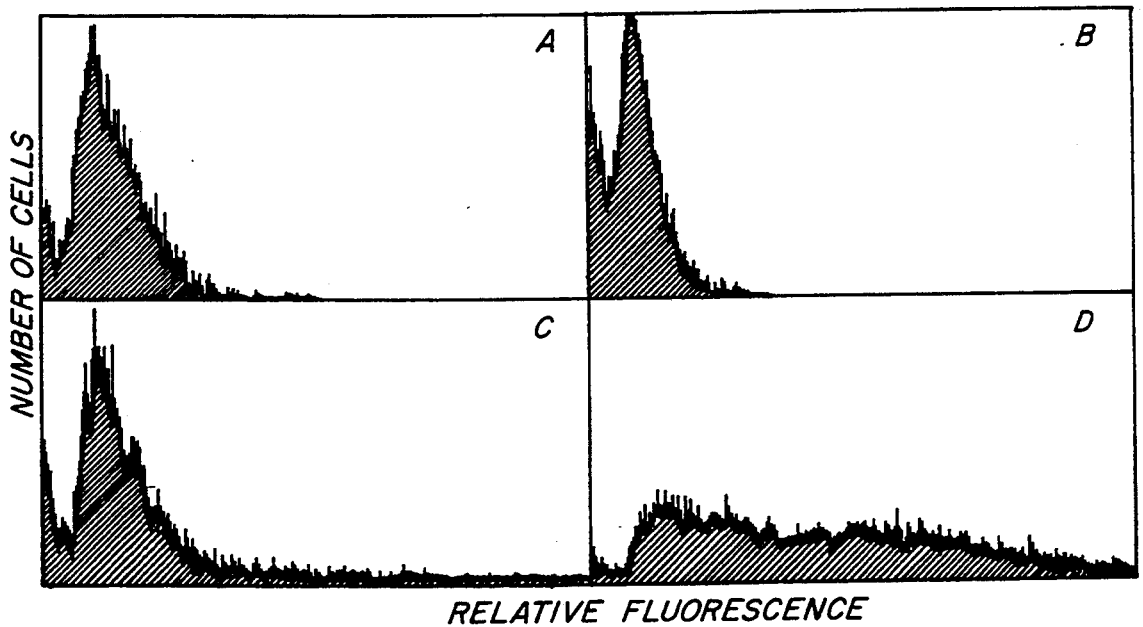
FIG. 13 is a graph showing fluorescence profiles of cells infected with the retrovirus of FIG. 12.

NIH3T3 cells were infected with the U3LacZ virus at an M.O.I. of 1 NEO$^r$ CFU/cell and pools of clones containing the U3LacZ provirus were analyzed using the FACS-FDG. Fluorescence depends on levels of β-galactosidase expression, variation in uptake of FDG by cells and the length of the reaction time. FIG. 13A illustrates the expression of endogenous β-galactosidase observed in NIH3T3 cells. As expected β-galactosidase expression in cells derived from a pool of NEO$^r$ cells infected by the U3LacZ virus was similar, with fewer than 1% of cells expressing higher levels of β-galactosidase (FIG. 13C).

LacZ+ and LacZ− clones were isolated by sorting 4 independent pools of 500 NEO$^r$ colonies ($10^6$ cells each). LacZ− clones were isolated from among the 100 cells with the lowest fluorescence; whereas, LacZ+ clones were isolated following 2 cycles of FACS-FDG selection in which 100 cells having the highest fluorescence were selected, pooled, grown in mass culture and resorted. Cells sorted for high and low fluorescence were plated at clonal densities and analyzed for β-galactosidase expression. None of the LacZ− clones and approximately 70% of the clones isolated after two cycles of FACS-FDG enrichment expressed β-galactosidase as judged by X-Gal staining. Thus the overall enrichment through 2 cycles of sorting was 117 fold. On average, LacZ+ clones expressed approximately 10 fold higher levels of β-galactosidase as compared to LacZ− clones.

Fluorescence profiles of U3LacZ infected NIH3T3 cells during the first and second rounds of FACS sorting are shown in FIG. 13C and 13D. To exclude the possibility that FACS enriched for cells expressing higher levels of endogenous cellular β-galactosidase, approximately 100 NIH3T3 cells having the highest fluorescence were selected, grown in mass culture and reanalyzed. No significant enrichment for cells expressing higher levels of endogenous β-galactosidase was seen (FIG. 13B). Thus recovery of cells expressing higher levels of lacZ depended on infection by U3LacZ Southern analysis of proviruses in LacZ+ and LacZ− clones.

Figure 14:
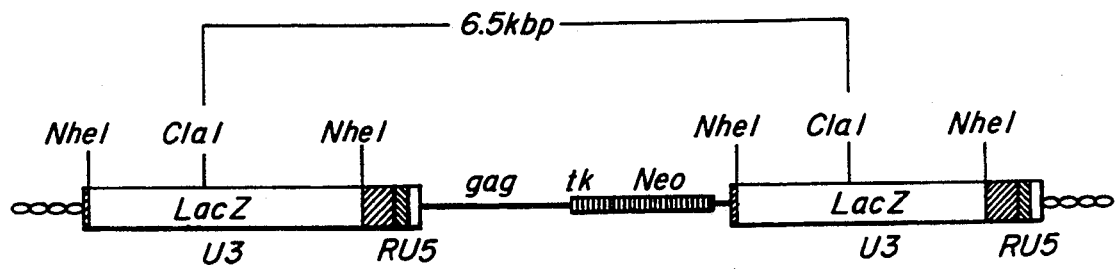
FIG. 14 is a schematic diagram of the genome of the provirus PGgTKNeoU3LacZen(−)

Structures of the integrated U3LacZ proviruses in each of 4 LacZ+ and LacZ− clones were analyzed by Southern blot analysis. Digestion of DNA from U3-LacZ infected clones with ClaI, which cuts once within the LTR, generated the 6.6 kb fragment expected if lacZ sequences duplicated as part of the LTR (FIG. 14).

Variable-sized fragments in different clones originate from ClaI sites in the flanking cellular sequences extending to the ClaI site in lacZ. Similarly, cleavage with EcoRI yielded expected fragments. These results indicate the 3.1 kb lacZ sequences inserted within U3 duplicate normally when the virus is passaged and (ii) activation of β-galactosidase does not require gross rearrangements of proviral sequences.

Cellular DNA was digested with HindIII (which does not cut within the provirus) and probed with lacZ and NEO to determine the number of proviruses per cell. Hybridization patterns for all clones were unique confirming that each was an independent isolate.

The ability to express β-galactosidase is not an intrinsic property of the provirus. Since only 0.6% of NEO$^r$ clones express β-galactosidase the ability to transduce a LacZ+ phenotype could be an intrinsic but inefficient property of each provirus. Alternatively, LacZ expression may require secondary events such as mutation or transcriptional activation by adjacent cellular DNA.

Several experiments suggested that the ability to express β-galactosidase is not an intrinsic property of the provirus. First, virus producer lines expressed low levels β-galactosidase, indicating that translation of 3′ lacZ sequences from polycistronic TKNeoLacZ transcripts does not occur at a significant level. Second, lack of β-galactosidase expression in LacZ− clones was phenotypically stable, e.g., the frequency with which LacZ− cells generated LacZ+ clones was less than $10^4$. However, conversion of LacZ+ into LacZ− phenotypes occured more frequently. Between 0.2-1% of colonies derived from several LacZ+ cell lines failed to stain with X-Gal.

Additional experiments suggest that β-galactosidase expression was not activated by mutations. First, the proviruses in LacZ+ lines lacked gross structural rearrangements as judged by Southern blot analysis. Second, viruses rescued from LacZ+ clones did not transduce β-galactosidase expression any more efficiently (as compared to their ability to transduce NEO$^r$) than the original U3LacZ virus.

LacZ expression is activated by flanking cellular promoters.

Figure 15:
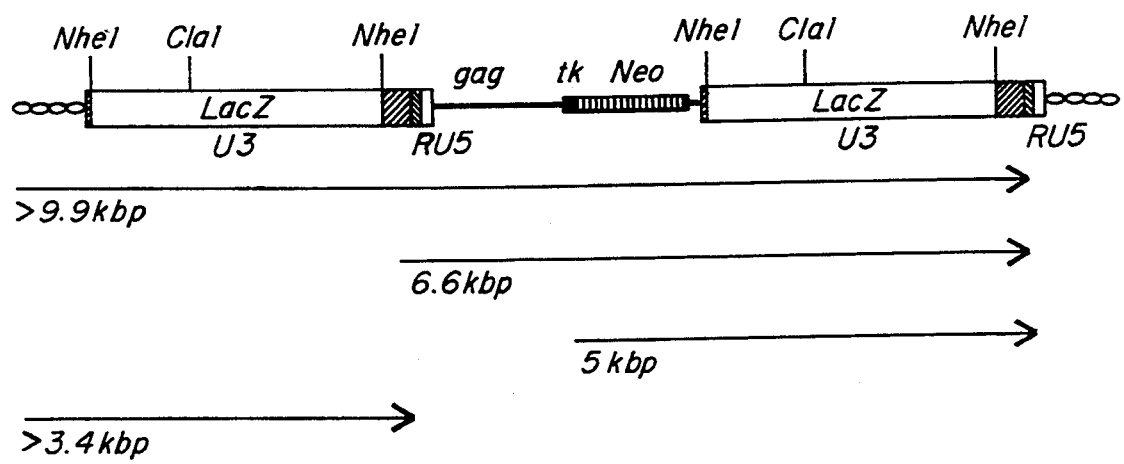
FIG. 15 is a schematic diagram of the genome of the provirus PGgTKNeoU3LacZen(−) analyzed by Northern blot hybridization.

To investigate whether β-galactosidase expression results from transcriptional activation of the lacZ by adjacent cellular sequences poly A+ selected RNA from LacZ+ and LacZclones was analyzed by Northern blot hybridization. All clones expressed 6.6 kb and 5 kb transcripts which hybridized to lacZ probes, however LacZ+ clones expressed two additional transcripts of 9.9 kb and 3.4 kb (FIG. 15). The presence of the 6.6 kb and 5 kb transcripts in all clones suggests that these initiate in the 5′ LTR and the tk promoter respectively and terminate in the 3′ LTR. Consistent with this model, the 9.9 kb, 6.6 kb and 5 kb transcripts hybridized to a neo probe, while only the 9.9 kb and 6.6 kb transcripts hybridized to gag. The two additional transcripts in LacZ+ clones appeared to initiate in the flanking cellular DNA and terminate at polyadenylation sites in the 3′ or 5′ LTR, respectively. The sizes of the 3.4 kb transcripts were never quite the same and varied by as much as 450 bp. This is the result one might expect if different lengths of cellular RNA became appended to lacZ depending on the location of the provirus downstream of a transcriptional promoter or within an exon. The LacZ− clone, W8A, also contains transcripts similar to those seen in LacZ+ clones. While the origins of these transcripts are unknown, ribonuclease protection analysis showed that they are not initiating in the flanking cellular DNA.

Figure 16:
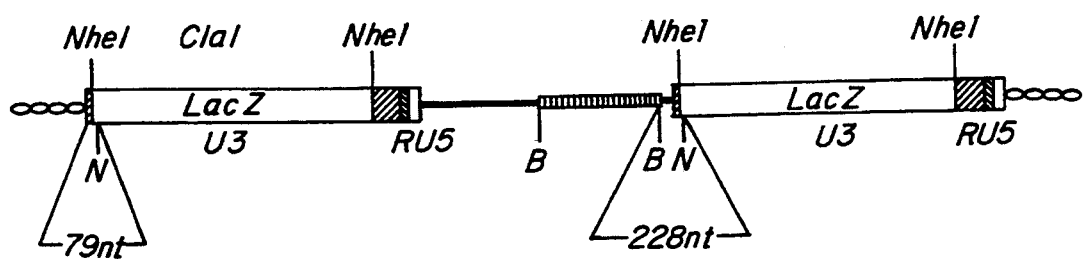
FIG. 16 is a schematic diagram of the genome of the provirus PGgTKNeoU3LacZen(−) analyzed by Protection assays.

To determine if transcripts in LacZ+clones initiate within flanking cellular DNA, total RNA was analyzed by an RNAase protection assay using $^{32}$P-labeled RNA probes complementary to the provirus coding strand extending from the BamHI and NruI sites of GgTKNeoU3LacZen(−). RNA from all clones protected a 228 bp fragment from polycistronic transcripts containing both the neo and 3' lacZ sequences. However only RNA from LacZ+clones protected a 79 bp fragment, the size expected for lacZ transcripts extending from the NruI site to the 5' end of the LTR. (FIG. 16)

Most LacZ+clones do not express fusion proteins.

Sequence analysis revealed that the translational reading frame upstream of LacZ is not blocked by termination codons. Consequently, β-galactosidase expression could result when the provirus integrates next to a promoter or in the appropriate translational reading frame in an exon. However, the electrophoretic mobilities of β-galactosidase proteins immunoprecipitated from LacZ+clones were similar to native β-galactosidase, indicating that most lacZ activating gene fusions do not append co-translated sequences to the 5' end.

EXAMPLE IV

Transgenic mice containing U3His proviruses may be derived by transferring totipotent histidinol resistant ES cell clones into preimplantation mouse blastocysts. Biological functions of the genes disrupted by the provirus may be assessed by inbreeding transgenic animals to obtain homozygous offspring. Disrupted genes associated with recessive phenotypes may be molecularly cloned using flanking sequence probes to screen genomic and cDNA libraries.

ES cell insertional mutagenesis

ES are infected cells with U3HIS viruses and HIS$^r$ cell lines are isolated. The male embryonal stem cell line ES-D3 derived from 129/SV +/+(agouti) mimics embryonal development in vitro and frequently contributes to germ line cells when injected into preimplantation embryos ([37, 38, 39, 40, 41, 42]. Since only totipotent ES cells form germ line chimeras, it is important to maintain this property during in vitro genetic manipulation. Consequently, ES cells must be grown in an environment that prevents differentiation, such as provided by feeder layers of mitotically inactivated mouse primary fibroblasts (MEF) or their clonal progeny (STO).

ES cells are grown on irradiated (3.2 Gy) primary mouse fibroblast or STO feeder layers. Feeder layer cells are seeded at $3 \times 10^6$ cells/60 mm dish (coated with 0.1% gelatin) and cultured overnight prior to the addition of ES cells. The growth medium is DMEM supplemented with 15% preselected and heat inactivated fetal bovine serum; 100 mM nonessential aminoacids, 0.1 mM β-galactosidase and 1000 U/ml LIF (Esgro$^R$). In general, $2 \times 10^5$-$1 \times 10^6$ ES cells are seeded per culture and passaged twice weekly onto fresh feeder layers. These conditions prevent ES cells from differentiating for at least 20 passages.

Infection with U3His viruses and isolation of Hisr clones $2 \times 10^5$ ES cells are infected at an MOI of 0.1 with GgU3HisTKneoen(−) virus prepared as described in Example I. High titer virustocks are obtained from the ecotropic producer line, ΨC9 [Example 1], which as assayed on NIH3T3 cells produces titers of $2 \times 10^6$ Neo CFU/ml and $1 \times 10^6$ His CFU/ml. ES cell clones surviving selection in 3 mM L-histidinol or 0.5 mg/ml G418 (concentrations previously found to kill 100% of ES cells within 4 days) are isolated and expanded on his- or neo-resistant STO feeder layers. Resistant STO cells are obtained by transfecting with pGgHisen(−) (retrovirus vector with an LTR driven his gene) or pSV2Neo, and isolating stable transformants in L-histidinol or G418. DNA is extracted from individual clones and analyzed by Southern blot hybridization to identify clones containing single provirus inserts and to isolate upstream flanking sequences by polymerase chain reaction.

Analysis of ES cell pluripotency

ES cells containing the U3His provirus are grown in Iscove's modified DMEM supplemented with 20% human cord blood serum (rich in erythropoietin) using bacterial plates and no feeder layers. Under these conditions ES cells grow in suspension and differentiate into cystic embryoid bodies after 5 days, develop heart muscle after 8 days and blood islands after 12 days. Those cell lines which develop beating heart and blood islands are most likely to also give rise to germ cells and are used for subsequent blastocyst injections.

Promoter trap vectors containing other selectable markers other than His may be used. Vectors containing hygromycin phosphotransferase and β-galactosidase inserted into U3 may involve less stringent selection conditions and, therefore, be more desirable.

Construction of germ line chimeras

To construct chimeric mice, ES cells homozygous for a coat color marker are injected into blastocysts of a recipient strain that lacks this marker, implanting the blastocysts into the uterus of outbred foster mothers and selecting chimeric offspring according to coat color [43]. Some chimeras when backcrossed to the blastocyst donor strain, produce offspring which exhibit coat color phenotypes encoded by the injected ES cells. This indicates that the injected ES cells have contributed to the formation of germ cells. Since the efficiency of germ cell chimericism and the percentage of germ cells derived from the donor cells is lower when cells of XX genotype are used, most laboratories employ male ES cells. The greatest efficiency in obtaining germ cells from pluripotential ES cells occurs when XY cells are transferred into XX recipient embryos. A high contribution by donor cells to the chimetic adult causes the donor cells to dominate sexual differentiation and the female embryo to develop as a phenotypic male. Under these circumstances no viable female germ cells can form from the recipient host cells and 100% of the germ cells are derived from the donor. This also causes the number of male offspring from chimetic blastocysts to be higher than expected.

HIS$^r$ D3-ES (XY, agouti/agouti) cells are injected into C57BL6 blastocysts which will be implanted into the Uterus of outbred albino CD1 mice, as described previously [43].

In general as the ES cells contain a single provirus per diploid genome, 50% of offspring from transgenic founder animals will be heterozygous for the his gene. To identify these mice, DNA is extracted from tail segments and analyzed by Southern blot hybridization. Mice carrying the U3His provirus will be inbred to produce F2 offspring of which 25% will be homozygous for the transgene. Mice may continue to be bred to homoygocity. Transgenic mice of this invention having abnormal phenotypes are identified, and the associated promoters and genes may be analyzed and sequenced. The developing transgenic embryos may be tested periodically to study gene regulation during development.

REFERENCES

The following publications, referred to above by number, are incorporated herein by reference:

1. Guild, B. C., M. H. Finer, D. E. Housman and R. C. Mulligan. 1988 J. Virology. 62: 3795-3801.
2. McNight, S. 1980. Nucl. Acid Res. 8: 5949-5964.
4. Mann, R., R. C. Mulligan and D. Baltimore. 1983. Cell. 33: 153-159.
5. Miller, A. D. and C. Buttimore. 1986. Mol. Cell. Biol. 6: 2895-2902.
6. Luthman, H. and G. Magnusson. 1983. Nucl. Acid. Res. 11: 1295-1307.
7. Maniatis, T. E., F. Fritsch and J. Sambrook. "Molecular Cloning: A Laboratory Manual." 1982 Cold Spring Harbor Laboratory. Cold Spring Harbor.
8. Feinberg, A. P. and B. Vogelstein. 1984. Annai. Biochem. 137: 266-267.
9. yon Melchner, H. and D. E. Housman. 1988. Oncogene. 2: 137-140.
10. Hartmann, S. C. and R. C. Mulligan. 1988. Pro. Natl. Acad. Sci. (USA). 85: 8047-8051.
11. Ehrlich, H. A., PCR Technology (Stockton Press, New York, 1989).
12. Reddy, S., Ozgur, K., Lu, M., Chang, W., Mohan, S. R., Kumar, C. C., Ruley, H. E., (1990), J. Biol. Chem. in press.
13. Burch, J. B. E., Evans, M. I., Friedman, T. M., O'Malley, P. J., (1988), Mol. Cell. Biol. 8, 1123-1131.
14. Hall, C., Jacob, E., Ringold, G., Lee, F., (1983), J. Mol. App. Genet. 2, 101-109.
15. Luthman, H., Magnusson, G., (1983), Nucl. Acid. Res. 11, 1295-1307.
16. Neumann, J. R., Morency, C. A., Russian, K. O., (1987), BioTechniques 5, 444-447.
17. Bradford, M., (1976), Anal. Biochem. 72, 248.
18. Miller, J. H., (Cold Spring Harbor Laboratory, Cold Spring Harbor, N.Y. 1972).
19. Guarente, L., Ptashne, M. , (1981), Proc. Nail. Acad. Sci. USA 78, 2199-2203.
20. Silver, J., Keerikatte, V., (1989), J. Virol 63, -1928.
21. Colicelli, Jr., Goff, S. P., (1985), Cell 42, 573-580.
22. Oeorgiev, G. P., (1984), Eur. J. Biochem. 145, -220.
23. Weiner, A. M., Deininger, P. L., Efstratiadis, A., (1986), Ann. Rev. Biochem.
24. J. Shine, L. Dalgarno, Proc. Natl. Acad. Sci. U.S.A. 71, 1342-1346 (1974).
25. J. A. Steitz, K. A. Jakes, Proc. Natl. Acad. Sci. U.S.A. 72, 4734-4738 (1975).
26. M. Kozak, Cell 44,283-292 (1986).
27. R. Mann, R. C. Mulligan, D. Baltimore, Cell 33, -159 (1983).
28. A.D. Miller, C. Buttimore, Mol. Cell. Biol. 6, -2902 (1986).
29. C. C. Shih, J. P. Stoye, J. M. Coffin, Cell 53, -537 (1988).
30. P. A. Norton, J. M. Coffin, Mol. Cell Biol., Vol. 5, pp 281-290 (1985).
31. G. P. Nolan, S. Fiering, J. F. Nicolas, L. A. Herzenberg, Proc. Natl. Acad. Sci. USA 85, 2603-2607 (1988).
32. T. Maniatis, E. F. Fritsch, J. Sambrook, Molecular cloning: a laboratory manual. Cold Spring Harbor Laboratory, Cold Spring Harbor, N.Y. (1982).
33. A. P. Feinberg, B. Vogelstein, Anal. Biochem. 137, 66-267 (1984).
35. H. von Melchner, H. E. Ruley, J. Virol. 63, 3227-3233 (1989).
36. H. von Melchner, S. Reddy, H. E. Ruley, Proc. Natl. Acad. Sci. USA 87, in press (1990).
37. Doetschman, T. C., H. Eistetter, M. Katz, W. Schmidt and R. Kemler. 1985. J. Embryol exp. Morph. 87: 27-45.
38. Gossler, A., T. Doetschman, R. Korn, E. Serfling and R. Kemler. 1986. Proc. Natl. Acad. Sci. USA. 83: 9065-9069.
39. Gossler, A., A. L. Joyner, J. Rossant and W. C. Skarnes. 1989. Science. 244: 463-465.
40. Joyner, A. L., W. C. Skarnes and J. Rossant. 1989. Nature. 338: 153-155.
41. Suda, Y., M. Suzuki, Y. Ikawa and S. Aizawa. 1987. J. Cell Physiol. 133: 197-201.
42. Zimmer, A. and P. Gruss. 1989. Nature. 338: 150-153.
43. Hogan, B., F. Constantini and E. Lacy. 1986. Manipulating the mouse embryo. A laboratory manual. Cold Spring Harbor Laboratory. Cold Spring Harbor, N.Y.

While specific embodiments have been shown above, the invention is not intended to be so limited. It should be understood that the foregoing description of the invention is intended merely to be illustrative thereof, and other embodiments, modifications and equivalents thereof may be apparent to those skilled in the art without departing from the scope or spirit of the invention.

Having thus described our invention, what is claimed is:

1. A retrovirus having a promoterless oligonucleotide coding for a protein located within a U3 or U5 control region of the retrovirus.
2. A retrovirus as claimed in claim 1 wherein the promoterless oligonucleotide coding for the protein is located within a U3 region.
3. A retrovirus as claimed in claim 2 wherein the promoterless oligonucleotide coding for the protein is located downstream of a U3 integration sequence and upstream of any U3 promoter sequence.
4. A retrovirus as claimed in claim 1 wherein the promoterless oligonucleotide coding for the protein is located within a U5 region.
5. A retrovirus as claimed in claim 1 wherein the protein is selected from the group consisting of thymidine kinase, beta-galactosidase, tryptophane synthetase, neomycin-phosphotransferase, histidinol-dehydrogenase, CD4, CD8, luciferase, chloroamphenecol-acetyltransferase, DHFR, HGPRT, and HYGRO.
6. A retrovirus as claimed in claim 1 wherein the retrovirus is enhancerless.
7. A retrovirus as claimed in claim 1 further comprising a second oligonucleotide coding for a protein located outside of the control regions and regulated by a promoter within the retrovirus.

8. A retrovirus as claimed in claim 1 wherein the retrovirus requires the presence of a helper virus for passage.

9. A retrovirus as claimed in claim 2 that is enhancerless.

10. A provirus having a promoterless oligonucleotide coding for a protein in its long terminal repeat (LTR).

11. A provirus as claimed in claim 10 wherein the promoterless oligonucleotide coding for the protein is located within a U3 region of the LTR.

12. A provirus as claimed in claim 10 wherein the promoterless oligonucleotide coding for the protein is located within a U5 region of the LTR.

13. A kit comprising
a container including a retrovirus having a promoterless oligonucleotide coding for a protein located within a U3 or U5 control region of the retrovirus, and
a container including a pair of polymerase chain reaction oligonucleotide primers complementary to portions of said promoterless oligonucleotide in a provirus corresponding to the retrovirus and capable of hybridizing to opposite sides of an enzymatic cleavage site of said promoterless oligonucleotide in said provirus.

14. A kit as claimed in claim 13 further comprising
a container including an enzyme capable of cleaving the provirus at the cleavage site.

* * * * *

UNITED STATES PATENT AND TRADEMARK OFFICE
CERTIFICATE OF CORRECTION

PATENT NO. : 5,364,783

DATED : November 15, 1994

INVENTOR(S) : H. Earl Ruley et al.

It is certified that error appears in the above-identified patent and that said Letters Patent is hereby corrected as shown below:

In column 1, as the first paragraph following the "Background of the Invention", insert --This invention was made with government support under contract number 5-P01-CA-42063; 5-P30-CA-14051 awarded by the National Institutes of Health. The government has certain rights in the invention.--

Signed and Sealed this

Twenty-first Day of February, 1995

Attest:

BRUCE LEHMAN

Attesting Officer

Commissioner of Patents and Trademarks